United States Patent [19]

Yamabe et al.

[11] Patent Number: 4,495,364
[45] Date of Patent: Jan. 22, 1985

[54] PROCESS FOR PRODUCING FLUORINATED ACID FLUORIDE HAVING ESTER GROUP

[75] Inventors: Masaaki Yamabe, Machida; Seiji Munekata, Tokyo, both of Japan

[73] Assignee: Asahi Glass Company Ltd., Tokyo, Japan

[21] Appl. No.: 121,479

[22] Filed: Feb. 14, 1980

Related U.S. Application Data

[63] Continuation of Ser. No. 847,908, Nov. 2, 1977, abandoned.

[30] Foreign Application Priority Data

Jul. 28, 1977 [JP]  Japan ............................... 52-89769

[51] Int. Cl.$^3$ ............................................. C07C 67/14
[52] U.S. Cl. ..................................... 560/180; 560/184
[58] Field of Search ................................ 560/180, 184

[56] References Cited

U.S. PATENT DOCUMENTS

Re. 29,534  2/1978  Resnick ........................... 260/543 F
3,250,807  5/1966  Fritz et al. ........................ 560/184

OTHER PUBLICATIONS

March, Jerry, Advanced Organic Chemistry, 2nd Ed., (1980) McGraw-Hill Publ., pp. 17-19, 320 and 803.
Groggins, P. H. "Unit Processes in Organic Synthesis" McGraw-Hill, Publ. 5th Ed., (1958), at p. 698.
Cason, James et al., *J. Org. Chem.* (1961), pp. 2024-2026, vol. 26.
House, Herbert O. "Modern Synthetic Reactions" W. A. Benjamin, Publ. 2nd. Ed., (1972), p. 302.
Tarrant, Paul "Fluorine Chemistry Reviews" Marcel Dekker, Publ., (1971), vol. 5, pp. 87, 90, and 95.
Malinovskii, M. S. "Epoxides and Their Derivatives" Israel Program for Scientific Translations, Publ., (1965), pp. 109, 123 and 158.
Kirk-Othmer "Encyclopedia of Chemical Technology" Interscience, Publ. 2nd Ed., (1969), vol. 16, p. 597.
Pauling, Linus "The Nature of the Chemical Bond" Cornell Univ. Press, Publ., (1948), pp. 64-67.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

A fluorinated acid fluoride having an ester group which has the formula

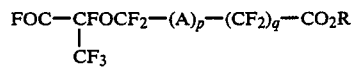

wherein A, p, q and R are defined below is produced by reacting a diacid fluoride having the formula

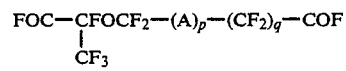

wherein A represents a $C_1$-$C_{10}$ bifunctional perfluoro group; p represents 0 or 1; q represents an integer of 1 to 8 with an alcohol having the formula ROH wherein R represents an organic group.

10 Claims, No Drawings

PROCESS FOR PRODUCING FLUORINATED ACID FLUORIDE HAVING ESTER GROUP

This is a continuation of application Ser. No. 847,908 filed Nov. 2, 1977, now abandoned.

BACKGROUND OF THE INVENTION

1. Field of the Invention:

The present invention relates to a process for producing a fluorinated acid fluoride having an ester group, more particularly, it relates to a novel process for producing a fluorinated acid flouride having an ester group by a reaction of a specific diacid fluoride with an alcohol.

2. Description of the Prior Arts

The flourinated acid flourides of the present invention have the formula

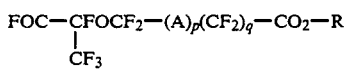

wherein A represents a $C_1$–$C_{10}$ bifunctional perfluoro group; p represents 0 or 1; q represents an integer of 1 to 8; and R represents an organic group.

The fluorinated acid fluoride having an ester group can be produced by the novel reaction of the specific diacid fluoride with an alcohol

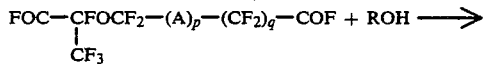

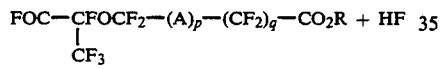

wherein A, p, q and R are defined above.

The monoesters of fluorinated acid fluoride produced by the process of the present invention are useful as intermediates for producing various fluorinated compounds especially various fluorinated compounds having a terminal ester group.

For example, perfluorovinyl ethers having an ester group can be obtained by the thermal decomposition of the monoesters of fluorinated acid fluoride as disclosed in Japanese Unexamined Patent Publication Nos. 83417/1977 and 105118/1977, etc.

The alkali metal salts of fluorinated carboxylic acid having an ester group can be obtained by reacting the fluorinated acid fluorides having an ester group with an alkali metal carbonate and the alkali metal salts can be thermally decomposed as disclosed in Japanese Unexamined Patent Publication Nos. 78826/1977 and 78827/1977.

The diacid fluorides used in the process of the present invention can be obtained by the reaction disclosed in Japanese Unexamined Patent Publication No. 3017/1977, etc.

The specific diacid fluorides can also be obtained by reacting α,ω-diiodo-perfluoroalkane or a perfluoro acid fluoride having a terminal iodo group with fuming sulfuric acid to obtain diacid fluorides disclosed in Japanese Unexamined Patent Publication Nos. 23020/1977 and 39605/1977 and then reacting the diacid fluoride with hexafluoropropylene epoxide.

The diacid fluorides can be also obtained by converting perfluorodicarboxylic acid dichlorides to difluorides in a polar solvent with NaF or KF and reacting the difluorides with hexafluoropropylene epoxide.

Alcohols as the other raw materials can be obtained from various sources as well-known. Usually, it is preferable to use the alcohols having the formula ROH wherein R is a group having 1 to 8 carbon atoms and can be in a straight chain form or a branched chain form.

The inventors have found that the acid fluorides having an ester group which have the formula FOC—CO$_2$R or FOC—A—CO$_2$R can be obtained by the reaction of dicarboxylic acid fluoride having the formula FOC—COF or FOC—(CF$_2$)$_n$—COF wherein n represents an integer of 1 to 10 with an alcohol having the formula ROH as disclosed in Japanese Patent Application No. 113712/1976.

The inventors have studied various reactions of the dicarboxylic acid difluorides with the alcohols. As the results, the interesting phenomenon of the present invention has been found.

The reactivity of carbonyl fluoride groups (—COF group) at both terminals to the alcohol is remarkably different depending upon the presence of —CF$_3$ group at the α-position to the carbonyl carbon.

The esterification with the alcohol is selectively performed for —COF group having no —CF$_3$ group at the α-position. In order to effectively and smoothly produce the monoesters of acid fluoride, it is preferable to use the specific asymmetrical diacid fluorides as the raw material.

In general, it is easily considered that perfluoro-2-methyl-3-oxa-heptanoyl difluoride having the formula

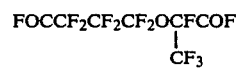

is an asymmetrical compound and the carbonyl carbons of the —COF groups at both terminals are expected to have different electrophilic property depending upon the presence of —CF$_3$ group at α-positions.

When the monoesterification with the alcohol is considered, the alkoxy group will attack the carbonyl carbon showing higher electrophillic character by —CF$_3$ group at the α-position, in a nucleophilic manner, whereby 1-carboalkoxy-perfluoro-2-methyl-3-oxa-hexanoyl fluoride having the formula

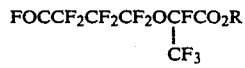

will be selectively produced.

The inventors have further studied the esterification in the system containing CsF, KF or NaF. As the results, the mole ratio of

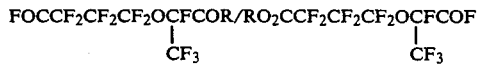

on the resulting product is 1/4.4 in the system of KF; and 1/6.1 in the system of NaF.

When the monoesterification is carried out in the system diluting the raw materials with the non-polar solvent, it has been found that the mole ratio of $$\text{FOCCF}_2\text{CF}_2\text{CF}_2\text{OCFCO}_2\text{R}/\text{RO}_2\text{CCF}_2\text{CF}_2\text{CF}_2\text{OCFCOF}$$
$$\overset{|}{\text{CF}_3} \qquad\qquad \overset{|}{\text{CF}_3}$$

is in a range of 1/18 to 1/50.

These descriptions are to clearly understand the present invention without any intention to limit the scope of the present invention.

SUMMARY OF THE INVENTION

It is an object of the present invention to provide a process for producing a fluorinated acid fluoride having an ester group in high efficiency and high yield by a selective reaction based on a substantially different reactivity of the carbonyl carbon.

The foregoing and other objects of the present invention have been attained by producing a fluorinated acid fluoride having an ester group which has the formula $$\text{FOC}-\underset{\overset{|}{\text{CF}_3}}{\text{CFOCF}_2}-(\text{A})_p-(\text{CF}_2)_q-\text{CO}_2\text{R}$$

wherein A represents a $C_1$-$C_{10}$ bifunctional perfluoro group; p represents 0 or 1; q represents an integer of 1 to 8; and R represents an organic group which comprises reacting a diacid fluoride having the formula $$\text{FOCCFOCF}_2-(\text{A})_p-(\text{CF}_2)_q-\text{COF}$$
$$\overset{|}{\text{CF}_3}$$

with an alcohol having the formula ROH.

DESCRIPTION OF THE PREFERRED EMBODIMENTS

In the present invention, the diacid fluoride as the raw materials have asymmetrical formulae wherein only one of the COF groups at both terminals is connected to a carbon atom which has —$CF_3$ group and the other —COF group is connected to carbon atom which does not have a —$CF_3$ group.

In the asymmetrical diacid fluorides having the formula $$\text{FOC}-\underset{\overset{|}{\text{CF}_3}}{\text{CFOCF}_2}-(\text{A})_p-(\text{CF}_2)_q-\text{COF}$$

A is a $C_1$-$C_{10}$ bifunctional perfluoro group preferably a $C_1$-$C_8$ bifunctional perfluoro group and A can be a straight chain or a branched chain having one or more ether bonds such as —$(CF_2)_n$—, $$-(\text{CFOCF}_2)_m- \quad \text{or} \quad -(\text{CFOCF}_2)_m-(\text{CF}_{23})_n-$$
$$\overset{|}{\text{CF}_3} \qquad\qquad \overset{|}{\text{CF}_3}$$

wherein n and m respectively represent 0 or an integer of 1 to 8. Usually, it is preferable to use the diacid fluoride wherein A is a $C_1$-$C_{10}$ bifunctional perfluoroalkylene group preferably a $C_1$-$C_8$ bifunctional perfluoroalkylene group; and P represents 0 or 1.

Suitable diacid fluorides include $$\text{FOCCFOCF}_2(\text{CF}_2)_4-\text{COF}$$
$$\overset{|}{\text{CF}_3}$$

$$\text{FOC}-\left(\underset{\overset{|}{\text{CF}_3}}{\text{CFOCF}_2}\right)_2-(\text{CF}_2)_2-\text{COF etc.}$$

The optimum results can be attained by using the diacid fluoride wherein p is 0 and q is 2, which has the formula $$\text{FOC}-\underset{\overset{|}{\text{CF}_3}}{\text{CFOCF}_2\text{CF}_2\text{CF}_2\text{COF}}.$$

As the alcohols having the formula ROH as the other raw material, it is preferable to use the alcohols wherein R is an alkyl group preferably a $C_1$-$C_{10}$ alkyl group especially a $C_1$-$C_5$ alkyl group.

The reaction of the specific diacid fluoride with the alcohol is preferably carried out under dilution with an inert organic solvent.

The reaction of the specific diacid fluoride with the alcohol is remarkably vigorous whereby it is preferable to carry out the reaction under the dilution with an inert organic solvent in order to selectively obtain the object of fluorinated acid fluoride.

The solvents used for the dilution should be inert to the alcohols, the diacid fluorides and the reaction products and should be liquid under the reaction conditions and miscible with the diacid fluoride and the alcohol and they are not critical.

Suitable solvents include $C_2$-$C_{12}$ hydrocarbon nitriles such as propionitrile, benzonitrile and acetonitrile; $C_4$-$C_{16}$ aliphatic and acyclic polyethers such as ethyleneglycol dimethyl ether, diethylene glycol dimethyl ether, triethyleneglycol dimethyl ether, tetraethyleneglycol dimethyl ether and dioxane.

In the process of the present invention, it is preferable to selectively produce the object compound by reacting the diacid fluoride with the alcohol while under using a non-polar solvent as a diluent. Suitable non-polar solvents include chlorofluoroalkanes and other haloalkanes such as trichloromonofluoromehtane, trichlorotrifluoroethane, and carbon tetrachloride.

In the dilution with the inert organic solvent, it is possible to select the ratio, and it is preferable to react them under diluting both of the diacid fluoride and the alcohol.

The dilution of the diacid fluoride is carried out at a ratio of the solvent to the diacid fluoride (ml/g) of about 0.1 to 10 preferably 0.3 to 3.0.

The dilution of the alcohol is carried out at a ratio of the solvent to the alcohol (g/g) of about 0.1 to 50 preferably 1.0 to 25.

It is possible to dilute one of the diacid fluoride and the alcohol before the reaction. It is also possible to gradually add the diacid fluoride and the alcohol into the inert organic solvent under stirring to form the uniform dilution in the reaction.

In order to increase the selectivity of the monoesterification, it is preferable to perform the reaction under dilution, especially the dilution of the alcohol.

The mole ratio of the alcohol to the diacid fluoride can be selected as desired, and it is preferably lower than 2.0 especially in a range of 0.5 to 1.5 in order to selectively obtain the object monoester of fluorinated acid fluoride.

In the present invention, it has been found that the selectively of the monoesterification is mainly dependent upon (1) the mole ratio of the alcohol to the diacid fluoride in the reaction, (2) the selection of the dilution with the inert organic solvent, (3) the kind of the solvent, and (4) the reaction conditions such as the reaction temperature whereby the object compound of

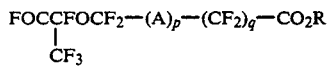

can be selectively obtained in comparison with the compound of

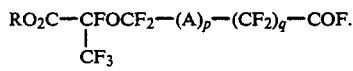

It is preferable to perform the reaction of the alcohol with the diacid fluoride under substantially anhydrous condition.

When water is remained, the corresponding dicarboxylic acid is formed by the reaction of the diacid fluoride with water or the reaction of the product having one mole of the ester with water, whereby the yield of the object monoester of fluorinated acid fluoride is lowered. Moreover, the corrosion of the reaction is disadvantageously promoted.

The reaction temperature is not critical. However, the reaction of the diacid fluoride with the alcohol is remarkably vigorous to cause the exothermic reaction whereby it is necessary to perform the reaction under the controlled conditions. It is suitable to react them at the reaction temperature of $-80°$ to $100°$ C., preferably $-40°$ to $50°$ C.

Thus, the formation of the diesters as disadvantageous by-products is controlled and also the formation of the other by-product of

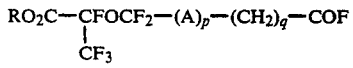

is controlled to obtain the object monoester of fluorinated acid fluoride in high yield.

In the process of the present invention, as shown in the reaction formula, hydrogen fluoride is formed as the by-product in the reaction of the alcohol with the diacid fluoride. The hydrogen fluoride can be easily separated by a distillation after the reaction. It is possible to add a HF collector such as alkali metal fluoride into the reaction system so as to smoothly treat the by-product HF. However, sometimes, the selectivity of the object monoester of fluorinated acid is lowered by the addition of a HF collector such as alkali metal fluoride.

The separation of HF such as stripping can be easily attained by using a non-polar solvent such as trichlorotrifluoroethane and the solid component is not included in the reaction system so as to easily attain the purification and separation of the subject monoester of fluorinated acid fluoride.

The reactors are preferably made of metal such as nickel and copper especially the vessel made of stainless steel or Hastelloy lining. The reactor made of glass cannot be used because of the by-product hydrogen fluoride. It is necessary to select the material of the reactor which is not corroded with HF.

The reaction of the present invention is preferably performed under the substantially anhydrous condition. The raw materials, the inert organic solvents and the reactors are preferably dried by suitable dehydrating method and the drying methods before using them.

The process of the present invention can be carried out by various operations under various conditions. It is possible to react them after charging the specific amounts of the alcohol and the diacid fluoride into the reactor. It is preferable to gradually add a solution of the alcohol diluted with the specific amount of the inert organic solvent into a solution of the diacid fluoride diluted with the specific amount of the inert organic solvent while controlling the reaction temperature.

In order to smoothly perform the reaction and to selectively obtain the monoester of fluorinated acid fluoride, it is preferable to employ a uniform mixing means for vigorously stirring the reaction system.

After the reaction, if necessary, the reaction mixture is filtered to remove the solid component from the reaction mixture and the filtrate is distilled to separate the object compound.

The invention will be further illustrated by certain specific examples which are included for purposes of illustration only and not intended to be limiting unless otherwise specified.

EXAMPLE 1

In a 300 cc autoclave made of stainless steel, 50 g of $FOC(CF_2)_3OCF(CF_3)COF$ and 50 ml of trichlorotrifluoroethane (R-113) were charged. The temperature in the autoclave was kept in $-10°$ C. and a solution of methanol in trichlorotrifluoroethane (concentration of methanol 20 wt. %) was added to it under vigorously stirring to give 1.15 of a mole ratio of methanol/-$FOC(CF_2)_3OCF(CF_3)COF$.

After the reaction, the reaction mixture was analyzed by the gaschromatography method and $^{19}F$ NMR method. The results are as follows.

Conversion of $FOC(CF_2)_3OCF(CF_3)COF$: 87.2%
Selectivity of $CH_3O_2C(CF_2)_3OCF(CF_3)COF$: 82.0%
Selectivity of $FOC(CF_2)_3OCF(CF_3)CO_2CH_3$: 2.8%
Selectivity of $CH_3O_2C(CF_2)_3OCF(CF_3)CO_2CH_3$: 15.2%

EXAMPLE 2

In accordance with the process of Example 1, the starting materials and the solvent were charged and a solution of methanol in trichlorotrifluoroethane (concentration of methanol 5.5 wt. %) was added to give 0.99 of the mole ratio of methanol/$FOC(CF_2)_3OCF(CF_3)COF$ in the reaction.

The results are as follows.
Conversion of $FOC(CF_2)_3OCF(CF_3)COF$: 93.4%
Selectivity of $CH_3O_2C(CF_2)_3OCF(CF_3)COF$: 84.5%
Selectivity of $FOC(CF_2)_3OCF(CF_3)CO_2CH_3$: 1.7%
Selectivity of $CH_3O_2(CF_2)_3OCF(CF_3)CO_2CH_3$: 13.8%

EXAMPLE 3

In the autoclave of Example 1, 50 g of $FOC(CF_2)_3OFC(CF_3)COF$ and 50 ml of diethleneglycol dimethyl ether were charged and the temperature in the autoclave was kept in $-10°$ C. and a solution of methanol in diethleneglycol dimethyl ether (concentration of methanol 12.5 wt. %) was added to it under vigorously stirring to give 1.11 of a mole ratio of methanol/-$FOC(CF_2)_3OCF(CF_3)COF$ in the reaction.

The results are as follows.

Conversion of $FOC(CF_2)_3OCF(CF_3)COF$: 94.0%
Selectivity of $CH_3O_2C(CF_2)_3OCF(CF_3)COF$: 75.0%
Selectivity of $FOC(CF_2)_3OCF(CF_3)CO_2CH_3$: 7.5%
Selectivity of $CH_3O_2C(CF_2)_3OCF(CF_3)CO_2CH_3$: 17.5%

EXAMPLE 4

In the autoclave of Example 1, 50 g of $FOC(CF_2)_3OCF(CF_3)COF$ and 50 ml of diethyleneglycol dimethyl ether and 11.7 of sodium fluoride (pure grade) were charged and the temperature in the autoclave was kept in $-10°$ C. and a solution of methanol in diethyleneglycol dimethyl ether (concentration of methanol 12.5 wt. %) was added to it under vigorously stirring to give 1.06 of a mole ratio of methanol/$FOC(CF_2)_3OCF(CF_3)COF$ in the reaction.

The results are as follows.

Conversion of $FOC(CF_2)_3OCF(CF_3)COF$: 88.2%
Selectivity of $CH_3O_2C(CF_2)_3OCF(CF_3)COF$: 72.6%
Selectivity of $FOC(CF_2)_3OCF(CF_3)CO_2CH_3$: 11.7%
Selectivity of $CH_3O_2C(CF_2)_3OCF(CF_3)CO_2CH_3$: 15.7%

EXAMPLE 5

In the autoclave of Example 1, 50 g of $FOC(CF_2)_3OCF(CF_3)COF$ and 50 ml of trichlorotrifluoroethane were charged and the temperature in the autoclave was kept in $-10°$ C. and a solution of ethanol in trichlorotrifluoroethane (concentration of ethanol 12.5 wt. %) was added to it under vigorous stirring to give 1.15 of a mole ratio of ethanol/$FOC(CF_2)_3OCF(CF_3)COF$ in the reaction.

The results are as follows.

Conversion of $FOC(CF_2)_3OCF(CF_3)COF$: 94.2%
Selectivity of $C_2H_5O_2C(CF_2)_3OCF(CF_3)COF$: 83.2%
Selectivity of $FOC(CF_2)_3OCF(CF_3,CO_2C_2H_5)$: 1.5%
Selectivity of $C_2H_3O_2C(CF_2)_3OCF(CF_3)CO_2C_2H_5$: 15.3%

EXAMPLE 6

In the autoclave of Example 1, 50 g of $FOC(CF_2)_3OCF(CF_3)CF_2OCF(CF_3)COF$ and 50 ml of trichlorotrifluoroethane were charged and the temperature in the autoclave was kept in $-5°$ C. and a solution of methanol in trichlorotrifluoroethane (concentration of methanol 12.5 wt. %) was added to it under vigorously stirring to give 1.05 g of a mole ratio of methanol/-$FOC(CF_2)_3OCF(CF_3)CF_2OCF(CF_3)COF$ in the reaction.

The results are as follows.

Conversion of $FOC(CF_2)_3OCF(CF_3)CF_2OCF(CF_3)COF$: 87.3%
Selectivity of $CH_3O_2C(CF_2)_3OCF(CF_3)CF_2OCF(CF_3)COF$: 81.3%
Selectivity of $FOC(CF_2)_3OCF(CF_3)CF_2OCF(CF_3)CO_2CH_3$: 2.3%
Selectivity of $CH_3O_2C(CF_2)_3OCF(CF_3)CF_2OCF(CF_3)CO_2CH_3$: 6.4%

REFERENCE 1

In an autoclave made of stainless steel, 162 g (3.85 mole) of sodium fluoride (highest grade) was charged and dried and then 150 ml of dehydrated diethyleneglycol dimethyl ether was charged. After cooling the autoclave with liquid nitrogen and then 146 g (1.56 mole) of oxalyl fluoride (FOC.COF) in a gaseous form was charged into the autoclave.

The temperature in the autoclave was kept in $-8°$ to $0°$ C. and a solution of ethanol in diethyleneglycol dimethyl ether (ratio of diethyleneglycol dimethyl ether/ethanol=3/1 by weight) was continuously fed under vigorously stirring to complete the reaction at b 1.03 of a mole ratio of ethanol to oxalyl fluoride.

The slurry in the autoclave was filtered to remove the solid components in the reaction mixture and the filtrate was distilled to obtain ethoxalyl fluoride ($FOC$—$CO_2C_2H_5$) having a boilingpoint of 46° to 48° C./90 mmHg at a yield of 69 mole % (based on oxalyl fluoride).

REFERENCE 2

In accordance with the process of Reference 1 except using methanol instead of ethanol, the reaction was continued to give 0.7 of the mole ratio of methanol to oxalyl fluoride and the reaction mixture was filtered and the filtrate was distilled to obtain 16 g of methoxalyl fluoride ($FOC$—$CO_2CH_3$) as the fraction of 48° to 50° C./200 mmHg.

REFERENCE 3

In an autoclave made of stainless steel, 208 g (4.95 mole) of sodium fluoride, 400 ml of dehydrated diethyleneglycol dimethyl ether and 400 g (2.06 mole) of perfluorosuccinic acid difluoride were charged, and a solution of ethanol in diethyleneglycol dimethyl ether (ratio of diethyleneglycol dimethyl ether/ethanol=3/1 by weight) was continuously fed at $-40°$ C. under vigorously stirring to complete the reaction at 1.1 of a mole ratio of ethanol to perfluorosuccinic acid difluoride.

The slurry in the autoclave was filtered to remove the solid components in the reaction mixture and the filtrate was distilled to obtain 3-carboethoxy perfluoropropionyl fluoride (b.p. 110° to 112° C./760 mmHg) at a yield of 66 mole % (based on perfluorosuccinic acid difluoride).

REFERENCE 4

In an autoclave made of stainless steel, 100 g (2.38 mole) of sodium fluoride, 200 ml of dehydrated diethyleneglycol dimethyl ether and 200 g (1.03 mole) of perfluorosuccinic acid difluoride were charged and a solution of ethanol in diethyleneglycol dimethyl ether (ratio of diethyleneglycol dimethyl ether to ethanol=9/1 by weight) was continuously fed at $-40°$ C. under vigorously stirring to complete the reaction at 1.2 of a mole ratio of ethanol to perfluorosuccinic acid difluoride.

In accordance with the process of Example 3, the product was separated to obtain 3-carboethoxy perfluoropropionyl fluoride at a yield of 75 mole % (based on perfluorosuccinic acid difluoride).

REFERENCE 5

In an autoclave made of stainless steel, 200 g (4.76 mole) of sodium fluoride, 400 ml of trichlorotrifluoroethane (R-113) and 400 g (2.06 mole) of perfluorosuccinic acid difluoride were charged and a solution of ethanol in R-113 (ratio of R-113 to ethanol=5/1 by weight) was continuously fed at −20° C. under vigorously stirring to complete the reaction at 1.2 of a mole ratio of ethanol to perfluorosuccinic acid difluoride.

In accordance with the process of Example 3, the product was separated to obtain 3-carboethoxy perfluoropropionyl fluoride at a yield of 52 mole % (based on perfluorosuccinic acid difluoride).

REFERENCE 6

In an autoclave made of stainless steel, 100 g (2.38 mole) of sodium fluoride, 200 ml of dehydrated diethyleneglycol dimethyl ether and 270 g (1.39 mole) of perfluorosuccinic acid difluoride were charged and a solution of methanol in diethyleneglycol dimethyl ether (ratio of diethyleneglycol dimethyl ether to methanol of 4/1 by weight) was continuously fed at −10° C. under vigorously stirring to complete the reaction at 1.1 of a mole ratio of methanol to perfluorosuccinic acid difluoride.

In accordance with the process of Example 3, the product was separated to obtain 3-carbomethoxy perfluoropropionyl fluoride (b.p. 97° C./mmHg) at a yield of 63 mole % (based on perfluorosuccinic acid difluoride).

REFERENCE 7

In an autoclave made of stainless steel, 100 g (2.38 mole) of sodium fluoride, 200 ml of diethyleneglycol dimethyl ether and 300 g (1.02 mole) of perfluoroadipic acid difluoride were charged and a solution of ethanol in tetraethyleneglycol dimethyl ether (ratio of tetraethyleneglycol dimethyl ether to ethanol of 3/1 by weight) was continuously fed at −10° C. under vigorously stirring to complete the reaction at 1.2 of a mole ratio of ethanol to perfluoroadipic acid difluoride.

The slurry in the autoclave was filtered to remove the solid components in the reaction mixture, and the filtrate was distilled to obtain 5-carboethoxy perfluoropentanyl fluoride (b.p. 68° to 70° C./30 mmHg) at a yield of 40 mole % (based on perfluoroadipic acid fluoride).

What is claimed is:

1. A process for producing a fluorinated acid fluoride having an ester group which has the formula $$FOC-\underset{CF_3}{CFOCF_2}-(A)_p-(CF_2)_q-CO_2R$$

wherein A represents a $C_1$-$C_{10}$ bifunctional perfluoro group; p represents 0 or 1 ; q represents an integer of 1 to 8; and R represents an organic group which comprises reacting a diacid fluoride having the formula $$FOC-\underset{CF_3}{CFOCF_2}-(A)_p-(CF_2)_q-COF.$$

with an alcohol having the formula ROH.

2. A process according to claim 1 wherein the reaction is carried out at a mole ratio of the alcohol to the diacid fluoride of less than 2.0.

3. A process according to claim 1 wherein the reaction is carried out under a dilution with an inert organic solvent.

4. A process according to claim 3 wherein said inert solvent is a nonpolar solvent.

5. A process according to claim 3 wherein the reaction is carried out under the dilution to be a ratio of the inert organic solvent to the diacid fluoride (ml/g) of 0.1 to 10.

6. A process according to claim 3 wherein the reaction is carried out under the dilution to be a ratio of the inert organic solvent to the alcohol (g/g) of 0.1 to 50.

7. A process according to claim 1 wherein the reaction is carried out at the reaction temperature of −80° C. to 100° C.

8. A process according to claim 1 wherein the reaction is carried out under substantially anhydrous condition.

9. A process according to claim 1 wherein the reaction is carried out in the presence of a hydrogenfluoride collector.

10. A process according to claim 9 wherein the hydrogenfluoride collector is a fluoride of an element of the I-A group of the periodic table.

* * * * *